United States Patent [19]

Bachenheimer et al.

[11] Patent Number: 4,607,526

[45] Date of Patent: Aug. 26, 1986

[54] PARTICLE ANALYSIS SYSTEM

[75] Inventors: Bernard O. Bachenheimer, Fairfield; Frank J. Antoci, Milford; Edward L. Carver, Jr., Naugatuck; Ernest N. Pellegrino, Bridgeport; Richard C. Seltenreich, Shelton, all of Conn.

[73] Assignee: Allied Corporation, Morris Township, Morris County, N.J.

[21] Appl. No.: 684,833

[22] Filed: Dec. 21, 1984

[51] Int. Cl.[4] .......................... G01N 15/10; G01N 15/12

[52] U.S. Cl. .......................... 73/432 PS; 73/864.81; 73/864.87; 251/129.17; 324/71.4; 422/103; 422/81; 377/12; 137/597; 137/872; 137/624.18

[58] Field of Search .................... 324/71.4; 73/432 PS, 73/432 R, 864.81, 864.83, 864.84, 864.85, 864.87; 422/103, 81, 82, 73; 377/12; 364/555; 251/129.17, 61.1; 137/597, 872, 637, 624.18

[56] References Cited

U.S. PATENT DOCUMENTS

| | | | |
|---|---|---|---|
| 3,057,376 | 10/1962 | Agutter et al. | 73/864.83 X |
| 3,417,605 | 12/1968 | Hahn | 73/864.83 X |
| 3,648,160 | 3/1972 | Beaver | 324/71.4 X |
| 3,690,833 | 9/1972 | Ferrari | 422/81 X |
| 3,787,026 | 1/1974 | Lazar | 251/61.1 X |
| 3,915,652 | 10/1975 | Natelson | 422/81 X |
| 4,103,229 | 6/1978 | Gear | 73/432 PS X |
| 4,119,120 | 10/1978 | Mehotty et al. | 251/61.1 X |
| 4,161,690 | 7/1979 | Feier | 324/71.4 |
| 4,274,452 | 6/1981 | Schmitt | 251/61.1 X |
| 4,283,262 | 8/1981 | Cormier et al. | 73/53 X |
| 4,304,257 | 12/1981 | Webster | 137/559 |
| 4,353,243 | 10/1982 | Martin | 251/61.1 X |

FOREIGN PATENT DOCUMENTS

| | | | |
|---|---|---|---|
| 2458545 | 6/1976 | Fed. Rep. of Germany | 73/864.81 |
| 2648751 | 5/1978 | Fed. Rep. of Germany | 422/103 |
| 14678 | 2/1981 | Japan | 251/129.17 |
| 651163 | 3/1979 | U.S.S.R. | 137/597 |

*Primary Examiner*—Stewart J. Levy
*Assistant Examiner*—Tom Noland
*Attorney, Agent, or Firm*—James Riesenfeld; Gerhard H. Fuchs

[57] ABSTRACT

A system that is particularly useful in biological fluid analysis includes a face plate member and a mating flexible member, one of which has a plurality of passages. Selected motion of the flexible member provides a valving action to control fluid flow into, through, and out of the passages. An analysis chamber in a surface of the face plate member is in fluid communication with a passage and has an analyzer which, for a hematology analyzer, is preferably an impedance-type particle counter.

7 Claims, 3 Drawing Figures

Air
11
10
27A
34
32
27B
14
33
V9
40
27
T14
V30
T17
15
V25
V26
V33
V28
Stock
Chamber
P2
V31
T17
T18
P1
V32
V34
V35
T19
V39
V40
42
40
41
41
50μl
Syringe
"D"
10ml
Syringe
Waste
25ml
Syringe

PARTICLE ANALYSIS SYSTEM

BACKGROUND OF THE INVENTION

1. Field of the invention

This invention relates to a system for particle analysis and, more particularly, to a fluidic system that uses a flexible diaphragm valve.

2. Description of the Prior Art

Systems for counting and analyzing particles suspended in a fluid find application in a variety of areas, particularly medical diagnostics. An early disclosure of an electrical method for detecting and counting particles in a fluid, where the fluid and particles have different electrical conductivities, was made in U.S. Pat. No. 2,656,508, issued Oct. 20, 1953, to W. H. Coulter. Since then, a large number of related patents and publications have appeared that involve improvements and/or refinements of the Coulter technique (see, e.g., U.S. Pat. No. 3,015,775, issued Jan. 2, 1962, to W. H. Coulter et al.). Basically, the technique involves monitoring the electrical impedance across a narrow gap as a dilute sample passes through the gap. The presence of a particle is indicated by a change in the impedance.

A valve that is useful in biological fluid handling systems was disclosed in U.S. Pat. No. 4,304,257, issued Dec. 8, 1981, to M. E. Webster. That valve involves two mating surfaces, one firm and one flexible. In one of the surfaces are channels, separated by lands that are coincident with the surface. For each pair of channels and the land that separates them, an actuator moves the flexible surface between one position, in which the flexible surface is sealed against the firm surface to prevent flow between the channels, and a second position, in which the flexible surface is spaced away from the first position to permit flow between the channels. The firm surface may be provided by a transparent material having a planar surface.

A system for analyzing a biological fluid was disclosed in U.S. Pat. No. 4,283,262, issued Aug. 11, 1981, to A. D. Cormier et al. The system comprises an analysis chamber, a measuring system connected to the analysis chamber, a flow network for connecting an inlet and an auxiliary fluid reservoir to the analysis chamber, and a pump between the analysis chamber and an outlet. The system may include valves of the type disclosed by Webster.

SUMMARY OF THE INVENTION

In accordance with the present invention, a valve and a system for particle analysis are provided. The valve comprises:

(a) a face plate member that has a substantially rigid surface, (b) a flexible sheet member that has a surface at least a part of which is adapted for mating engagement with a corresponding part of the face plate surface, (c) a plurality of channels in at least one of the members, (d) a valve land that separates at least two adjacent channels in a member in a region where the channels are substantially parallel, the land having a surface adapted for releasably mating with a corresponding part of the surface of the other member, and (e) a valve actuator associated with a valve land and adapted to flex the sheet member between a first position, in which the valve land of one member sealingly mates with the corresponding part of the surface of the other member, and a second position, in which the sheet member is spaced away from the first position to allow flow across the land and between the adjacent channels.

The system comprises:

(a) a face plate member that has a substantially rigid surface, (b) a flexible sheet member that has a surface at least a part of which is adapted for mating engagement with a corresponding part of the face plate surface, (c) a plurality of passages in at least one of the members, (d) a plurality of valve lands, each of which separates at least two adjacent passages in a member, the lands having surfaces adapted for releasably mating with corresponding parts of the surface of the other member, (e) a plurality of valve actuators, each associated with a valve land and adapted to flex the sheet member between a first position, in which the valve land of one member sealingly mates with the corresponding part of the surface of the other member, and a second position, in which the sheet member is spaced away from the first position to allow flow across the land and between the adjacent passages, (f) in the face plate member, at least one analysis chamber in fluid communication with at least one passage, (g) analysis means connected in sensing relation to each analysis chamber and adapted for analyzing particles in a fluid, (h) pump means for pumping fluid through the system, and (i) means for controlling the sequential operation of valve actuator and pump means.

A particular embodiment of the present invention provides a hematology analyzer that minimizes cell hemolysis. The hematology analyzer comprises a system as described above, in which the particle analysis means is an impedance-type particle counter.

Another embodiment of the present invention is a system for precise dilution of a fluid sample with a fluid diluent comprising (a) a face plate member that has a substantially rigid surface, (b) a flexible sheet member that has a surface at least a part of which is adapted for mating engagement with corresponding parts of the face plate surface, (c) a plurality of passages, including a network of channels in at least one of the members, (d) a positive-displacement fluid-metering device, external to the members, for accurately measuring a predetermined volume of fluid, (e) a passage, in communication with the fluid-metering device, for isolating the volume of fluid and for passing it to a channel of the network, (f) a plurality of valve lands, each of which separates at least two adjacent passages in a member, the lands having surfaces adapted for releasably mating with corresponding parts of the surface of the other member, (g) a plurality of valve actuators, each associated with a valve land and adapted to flex the sheet member between a first position, in which the valve land of one member mates with the corresponding part of the surface of the other member, and a second position, in which the sheet member is spaced away from the first position to allow flow across the land and between the adjacent passages, (h) a mixing chamber in fluid communication with at least one passage for mixing the fluid sample with the fluid diluent, (i) pump means for pumping fluid through the system, and (j) means for controlling the sequential operation of valve actuator and pump means.

The valve, particle analyzer, and dilution system of the present invention provide several advantages over prior art systems, primarily by reducing the amount of connecting tubing required. The units are compact, reliable, and easily serviced. They require only small volumes of fluid and can be cleared of previous fluids easily, with minimal carry-over.

DETAILED DESCRIPTION OF THE INVENTION

Figure 1:
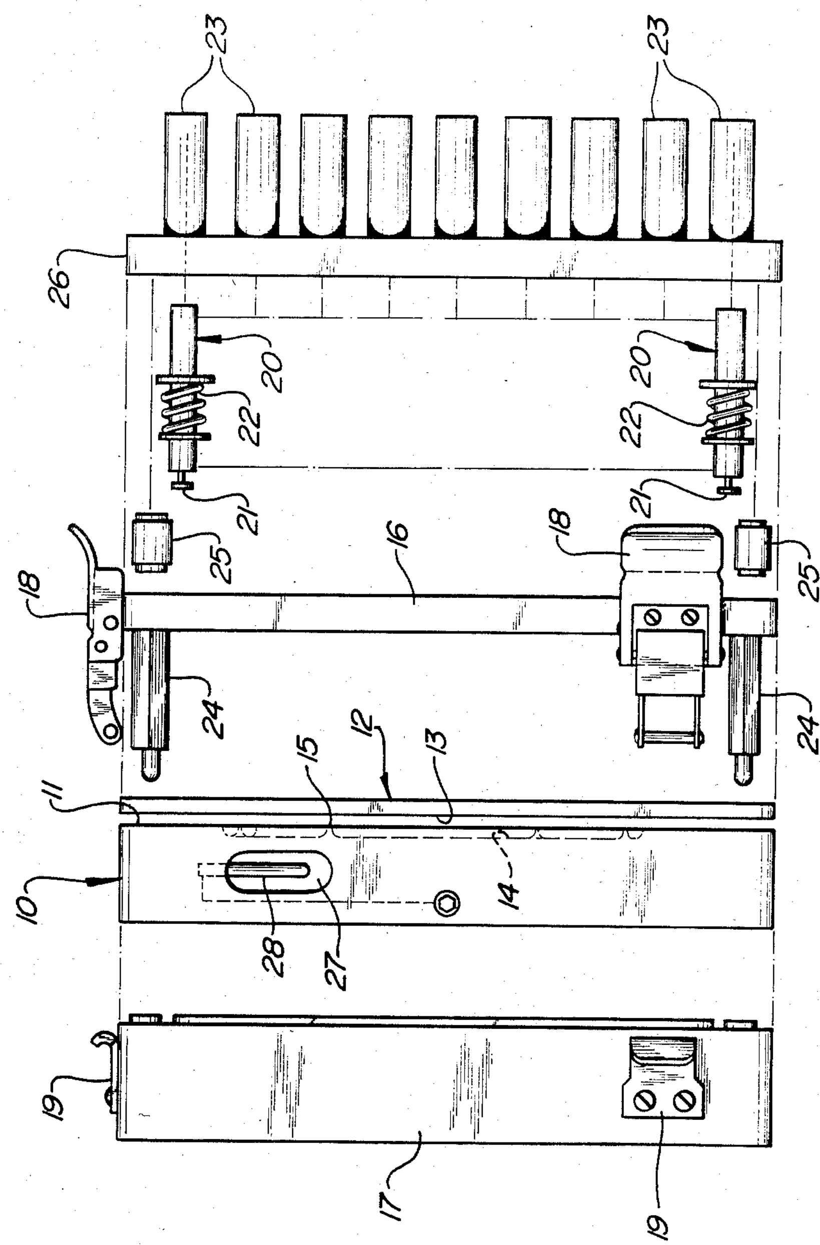
FIG. 1 is an exploded side view of a fluidic assembly of the present invention.

The present invention provides a system for analyzing particles in a fluid. In a typical application, the particles have electrical conductivity different from that of the fluid, and the particles are analyzed by monitoring the electrical impedance across a narrow gap through which the fluids, diluted if necessary, flows. The system is particularly adapted for analyzing particles in biological fluids, more particularly in blood.

In another enbodiment, the invention provides a system for precise dilution of a fluid, which can be a biological fluid such as blood. The preferred elements of the fluid dilution system are essentially the same as those of the particle analyzer, except that the fluid-dilution system need not include an analysis chamber and associated analysis means; the particle analyzer need not include a fluid-metering device or a conduit for isolating a predetermined volume of fluid. In the discussion below, the particle analyzer system is emphasized; however, the description applies equally to the fluid dilution system, except for the references to the analysis chamber/means elements. Of course, the fluid being diluted need not include particles.

Each system includes a face plate member, whose surface is rigid, and a flexible member. A plurality of passages is in at least one of the members; for example, a network of channels may be cut into the surface of one of the members, generally the face plate. The network provides a path for the various fluids to follow—sample, diluent, rinse, etc. Fluidic volumes are accurately and precisely measured by one or more positive displacement fluid-metering devices, preferably syringe pumps, the displacements of which are coupled to passages and to the network of channels by tubes and a multi-element connector. When they do not contain sample fluid, all elements of the measuring portion of the network are filled with an essentially incompressible fluid, such as water. A measured amount of fluid can be isolated in a passage, which can be either a conduit (a cylindrical passage in the body of the face plate) or a channel (a generally half-cylindrical passage in the face plate surface, covered by the flexible member). Conduits are preferred for containment, because fluid is less likely to be trapped in them.

The route and timing of the fluid flows are determined by the operations of pumps and valves. A typical particle analysis sequence, including optional dilution, involves the following steps:

1. Empty and rinse all passages and chambers.
2. Aspirate a fluid sample into the system.
3. Isolate a measured volume of sample.
4. Rinse passages surrounding the isolated sample.
5. Dispense diluent through and around sample to form a diluted sample in the mixing chamber.
6. Pass diluted sample to analysis chamber. (Optionally, isolate a measured volume of the diluted sample for further dilution).
7. Determine parameter(s) of interest.
8. Pass diluted sample to additional analysis chamber(s) and/or to waste.
9. Clean all passages and chambers Conventional methods, known in the art and possibly employing a computer, control the sequential operation of the valve actuators and pumps. Each valve operates by the motion of a section of the flexible member into and out of contact with a land on a corresponding section of the other member. Preferably, a land separates two or more channels in a region where two channels are substantially parallel, thus providing reduced turbulence and greater throughput.

The flexible sheet must, of course, be inert to the fluid it comes in contact with. In addition, depending on the particle and fluid being studied, it must have a smooth surface to avoid damaging the particles. Pressure molded silicone rubber is suitable, as are injection molded elastomers, which are preferred, because they are less expensive. Block copolymers, containing styrene, ethylene, or butylene styrene, optionally combined with silicone fluid, mineral oil, or polypropylene, are particularly suitable for hematology applications.

When the present system is used as a hematology analyzer, an element of an impedance-type particle counter is preferably mounted in an analysis chamber in the face plate member. Additional analysis/transducer elements, such as photometric devices etc., may also be part of the hematology analyzer. For hematology, it is important to avoid hemolysis. Therefore, the channels that carry whole or diluted blood are preferably between about 1.0 mm and 1.5 mm wide and between about 1.5 mm and 2.0 mm deep, with few, if any, sharp corners in the channel cross section and few, if any, sharp turns in the channel path. If the channels are narrower or shallower, flow rate is undesirably low. If they are deeper and/or wider, capillary action doesn't completely empty them. Ideally, fluids maintain a continuous stream and don't break into separated droplets. The preferred dimensions for sample-carrying channels are about 1.2 mm wide and 1.8 mm deep. Although other channels have different and/or less-stringent constraints, convenience will generally dictate making all channels of the same width. On the other hand, it is not inconvenient to fabricate channels of different depths.

Although turbulence facilitates mixing, it can also cause hemolysis and the introduction of small air bubbles. Thus, it is important to control fluid flow in chambers where blood samples are mixed or diluted. To accomplish this, it is desirable to limit the angle at which a channel inlet enters such a chamber to a preferred range of values. Specifically, the angle, in the plane of the face plate surface, that an entering channel makes with a tangent to the chamber at the point of entry is preferably between about 20° and 70°. Angles less than 20° tend to cause hemolysis and/or reduced flow rate. At angles less than 20° or greater than 70°, mixing is not very effective. Note that a mixing chamber may be separate from an analysis chamber or a single chamber may serve both purposes.

In essence, the analyzer of the present invention integrates a valving system and one or more analysis transducers to provide a compact system that is inexpensive to fabricate and that has a minimal amount of connecting tubing.

FIG. 1 depicts an exploded side view of a particle analyzer system of the present invention. The system comprises a face plate member or "porting block" 10, which has a rigid surface 11. Preferably, the porting block is transparent, so that system operation can be observed. Flexible sheet 12 has a surface 13, which is adapted to seal against selected areas of rigid surface 11. Channels 14 are typical of the channels in surface 11 that provide paths for conveying fluid through the system. Land 15, separating channels 14, is typical of lands that seal against surface 13 to block flow between passages. In the apparatus shown, surfaces 11 and 13 are both planar and are urged into sealing engagement by being sandwiched between backing plate 16 and clamping frame 17, which, in turn, are held together by off-center latches 18 and 19. The latches permit fast and easy manual removal of porting block 10 and frame 17 from flexible sheet 12 and backing plate 16. Valve actuators 20 have tips 21 that are demountably attached to flexible sheet 12 and are urged forward by the force of springs 22, thus sealing areas of surface 13 against areas of surface 11. When it is actuated, solenoid 23 provides a force that overcomes the forces of the spring and flexible sheet and moves surface 13 away from land 15, thus permitting fluid to flow across land 15 and between channels 14. (See the broken-out section of the valve actuator assembly in FIG. 2.) Spacers 24 and 25 maintain the separation of backing plate 16 from clamping frame 17 and solenoid mounting plate 26, respectively. Mounted in analysis chamber 27 is a portion, 28, of the analysis means, shown here schematically. In a preferred embodiment, 28 is an electrode for an impedance-type particle counter.

Figure 2:
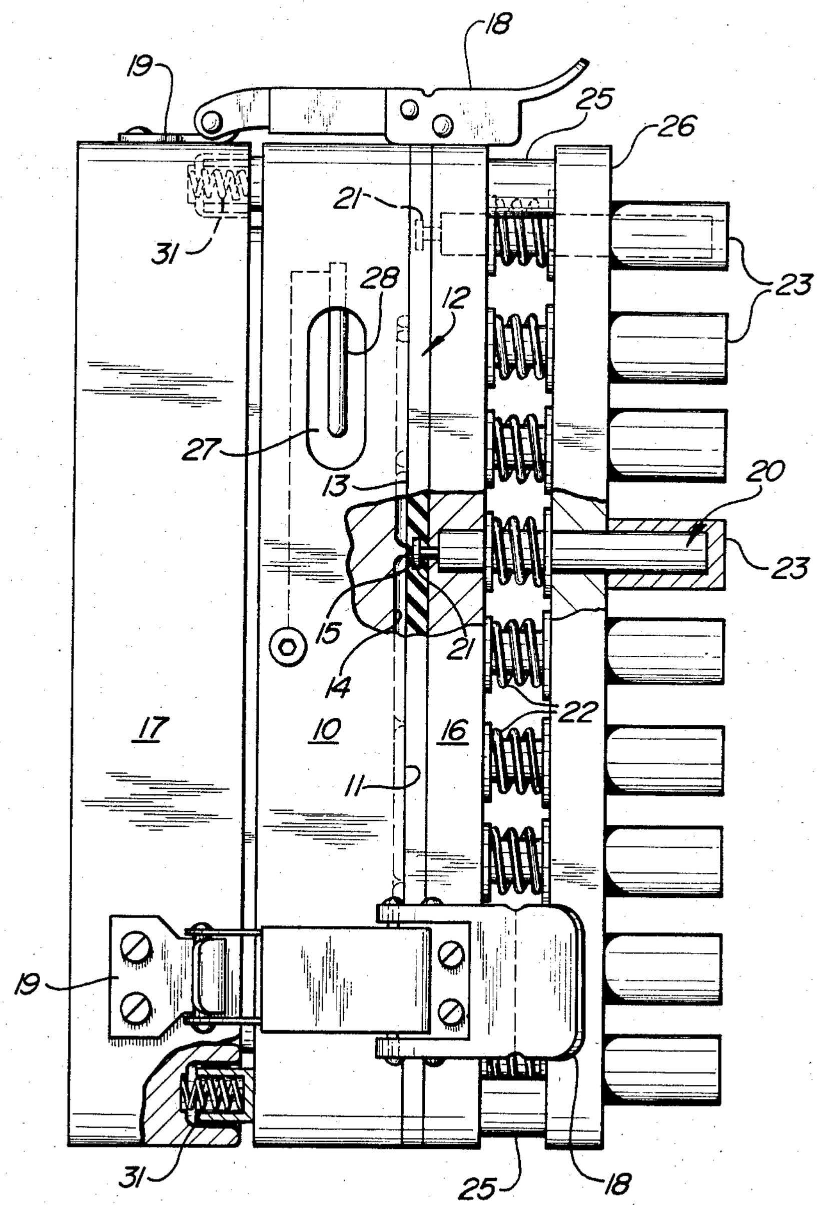
FIG. 2 is a side view in partial cross section of a fluidic assembly.

FIG. 2 depicts a side view of a fluidic assembly, including a spring-loaded frame 17, in which one of the springs 31 is shown in cross section.

Figure 3:
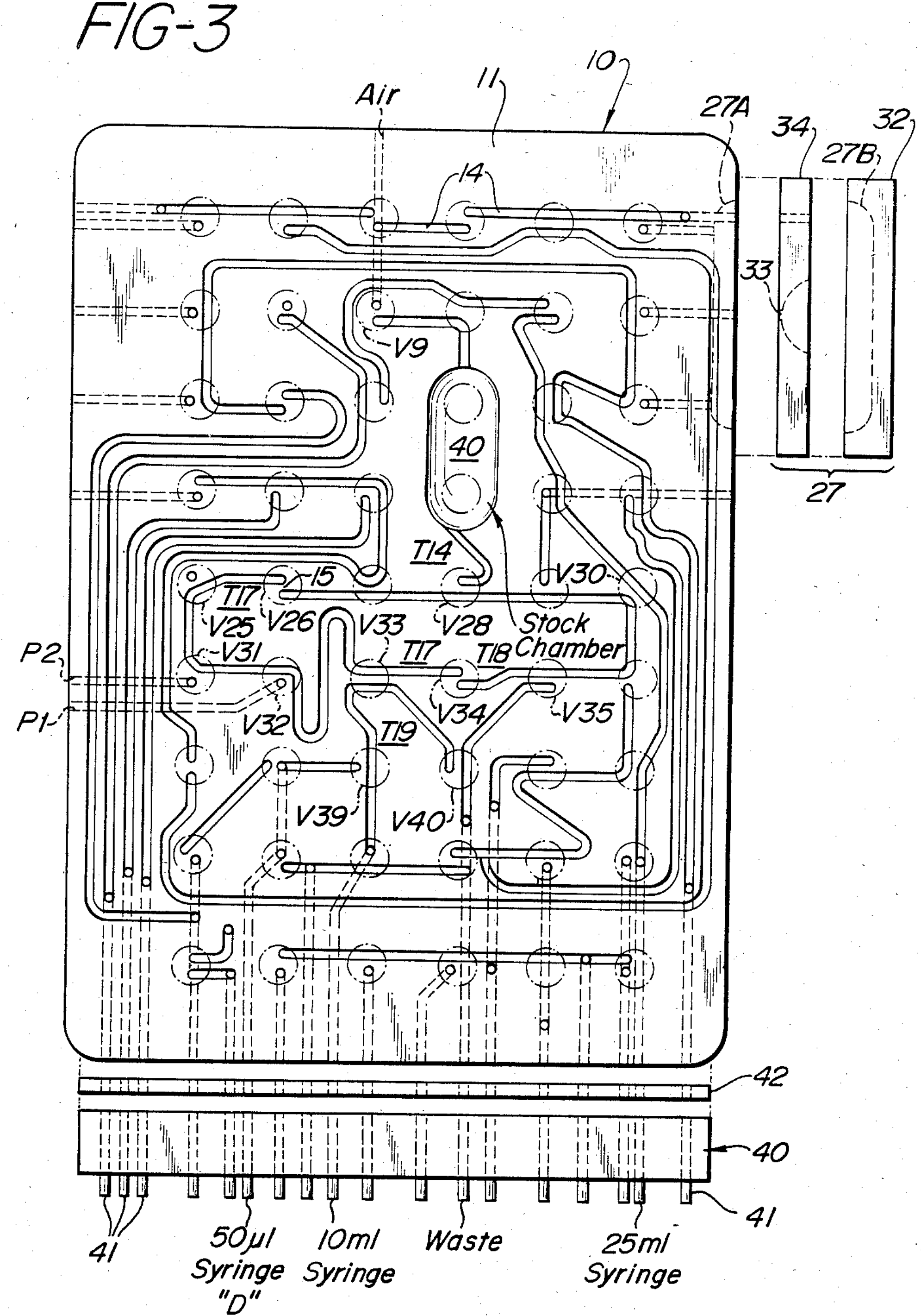
FIG. 3 is an exploded elevational view of a porting block of the present invention, together with adjoining analysis chamber and fluidic connector.

FIG. 3 is an exploded elevational view that depicts the main elements of a fluid (blood) dilution and analysis system. It shows the face plate member, or porting block, including valve sites, interconnecting passages, inlets, and outlets. It also shows exploded views of a particle analysis means and a multi-terminal fluidic connector.

Multi-terminal fluidic connector 40 has multiple fittings, such as 41, to provide inlets to and outlets from the porting block. Although shown in an exploded view for clarity, gasket 42 is actually in sealing engagement with fluid connector 40 on one face and with the bottom surface of porting block 10 on the other. Thumb screws (not shown) provide convenient means for fastening connector 40 to porting block 10. Of course, paths through connector 40 and gasket 42 are aligned with the inlets to the porting block. Instead of gasket 42, seals can be provided by O-rings or other means well known in the art.

Preparation of a diluted blood sample is accomplished as follows:

A whole blood sample is presented to the aspirator tube connected to port 2 (P2) of the porting block. A 100 μl sample of whole blood is aspirated via the 10 ml syringe by opening V31 and V33. The sample is transferred up the tube into port 2, through V31 and past V32, and is then stopped half-way between V32 and V33. V31 and V33 are then closed. The leading edge and approximately 40% of the 100 μl sample are used to precondition T17 (between V31 and V33) before a measured (10.12 μl)sample of whole blood is aspirated at V32. The aspiration of whole blood for the measured sample is done by first opening V25, which allows air to enter as the blood enters a conduit at V32. V32, which is connected to the 50 μl syringe via port 1 (P1), is then opened. The 50 μl syringe measures/aspirates the 10.12 μl sample of blood, which is then diluted as follows:

At the completion of the syringe move, V32 is closed and the sample is enclosed in port 1. Rinsing and filling of the dilution circle (T17 and T18) are the next steps. However, before rinsing and filling the dilution circle, the stock chamber 40 must be emptied of its contents. This is accomplished by opening V9, V28, and V30. The 25 ml syringe then aspirates out the contents of the stock chamber. At the end of the syringe move, V9, V28, and V30 are closed.

To rinse and fill the dilution circle, V33, V26, and V35 are opened. The 10 ml syringe then dispenses sufficient diluent to rinse away all remaining blood in T17 through T18 and out V35 to waste. At the end of the syringe move, V26 is closed and V34 is opened. The 10 ml syringe again dispenses diluent through V33 out to waste via V35. At the end of the syringe move, V33 and V34 are closed, V40 is opened, and the 10 ml syringe dispenses sufficient diluent to fill T19 via V40, which is connected to waste. This completes the rinsing and filling of the dilution circle.

At this time, both the 50 μl syringe and the 10 ml syringe, as well as their associated tubing, are completely filled with diluent. The end of port 1 contains the 10.12 μl sample of whole blood. The blood sample is diluted by first opening valves V39, V32, V26, V28, and V9. The 10 ml syringe then dispenses 2.5 ml of diluent, which flows from the 10 ml syringe through V39 to the D connection of the 50 μl syringe, out the top of the 50 μl syringe, through port 1, V32, T17, V26, T18, V28, and T14 into the stock chamber. V9 acts as a vent to atmosphere as the stock chamber is being filled. This flow of diluent carries the majority of whole blood into the stock chamber.

Channel T14 enters the stock chamber at a 60° angle from the horizontal center line of the stock chamber for the reasons discussed above. The chamber is bathtub-shaped and is cut directly into the porting block. The central section of the chamber is cylindrical, with the bottom area a recessed quarter of a sphere. A swirling action is induced when fluid is injected into the mixing (stock) chamber. The swirling action produces a relatively homogeneous mixture, with minimal introduction of air into the mixture. As the flow begins, a portion of the whole blood goes into the diluent in T17, between V32 and V34. Also, a portion of the whole blood sample goes into the diluent past V28; the balance goes through V28 and enters the stock chamber. To ensure that all the whole blood goes into the stock chamber, the following occurs: After approximately 1.5 ml of diluent has passed through V32, which assures that port 2 no longer contains any whole blood, V33 is opened and V32 and V39 are closed. Diluent is then allowed to flow through V33 through T17, V26, T18, and V28 into the stock chamber. This adds back to the stock dilution that portion of whole blood which had previously been between V32 and V34. Next, V34 is opened and V26 is closed, which adds back to the stock dilution that portion of whole blood that went past V28 due to the initial move of diluent and whole blood. When the 10 ml syringe is through dispensing the required diluent, all valves are closed. The appropriate dilution has been made and is contained within the stock chamber.

Analysis of the blood sample is done in analysis chamber 27, which includes section 27A in porting block 10 and section 27B, housed in block 32, adjacent to the porting block. The sections are separated by small aperture 33 in elastomeric plate 34. An electrode (not shown) is mounted in each of the two sections for monitoring impedance. A particle passing through aperture 33 is detected, because the impedance changes. Though shown in an exploded view, plate 34 is sealingly sandwiched between blocks 10 and 32.

We claim:

1. A system for particle analysis comprising:

(a) a face plate member that has a substantially rigid surface, (b) a flexible sheet member that has a surface at least a part of which is adapted for mating engagement with a corresponding part of the face plate surface, (c) a plurality of passages in at least one of the members, (d) a plurality of valve lands, each of which separates at least two adjacent passages in a member, the lands having surfaces adapted for releasably mating with corresponding parts of the surface of the other member, (e) a plurality of valve actuators, each associated with a valve land and adapted to flex the sheet member between a first position, in which the valve land of one member sealingly mates with the corresponding part of the surface of the other member, and a second position, in which the sheet member is spaced away from the first position to allow flow across the land associated therewith and between the adjacent passages that are separated therby when said sheet member is in said first position, (f) in the face plate member, at least one analysis chamber in fluid communication with at least one passage, (g) analysis means connected in sensing relation to each analysis chamber and adapted for analyzing particles in a fluid, (h) pump means for pumping fluid through the system, and (i) means for controlling the sequential operation of the valve actuators and pump means.

2. The system of claim 1, in which the passages include a network of channels and further comprising a positive-displacement fluid-metering device, external to the network, for accurately measuring a predetermined volume of fluid, and in which at least one of the passages is a conduit, in communication with the fluid-metering device, for isolating the volume of fluid and for passing it to a channel of the network.

3. The system of claim 1 further comprising a multi-terminal fluidic connector for providing fluid communication between the passages and a plurality of tubes, external to the system.

4. The system of claim 1 in which the particle analysis means is an impedance-type particle counter and wherein said system is at least a part of a hematology analyzer.

5. The system of claim 4, in which the passages include a network of channels and the channels have a width in the range from about 1.0 mm to about 1.5 mm, a depth from about 1.5 mm to about 2.0 mm, and a smooth cross section.

6. The system of claim 4 in which the sheet member comprises an injection-molded elastomer.

7. The system of claim 4 further comprising, in the rigid face plate surface, a vertically-oriented mixing chamber, having a bottom half and a top half, in fluid communication in its bottom half with an inlet channel whose intersection with the plane of the surface forms a line that enters the chamber at a point and that forms, in the plane of the surface, an angle of between 20° and 70° with a tangent to the chamber at that point.

* * * * *